(12) United States Patent
Raisanen

(10) Patent No.: US 6,786,076 B2
(45) Date of Patent: Sep. 7, 2004

(54) THIN FILM GAS SENSOR

(75) Inventor: Walfred R. Raisanen, Harriman, TN (US)

(73) Assignee: Reliable Instruments LLC, Harriman, TN (US)

( * ) Notice: Subject to any disclaimer, the term of this patent is extended or adjusted under 35 U.S.C. 154(b) by 0 days.

(21) Appl. No.: 10/306,444

(22) Filed: Nov. 25, 2002

(65) Prior Publication Data

US 2004/0099047 A1 May 27, 2004

(51) Int. Cl.[7] .............................................. G01N 27/12
(52) U.S. Cl. ...................... 73/31.05; 73/25.05; 422/88; 422/98
(58) Field of Search ............................... 73/23.2, 23.31, 73/24.06, 25.05, 31.05; 422/88, 90, 96, 98

(56) References Cited

U.S. PATENT DOCUMENTS

| | | |
|---|---|---|
| 3,714,562 A | 1/1973 | McNerney |
| 4,953,387 A | 9/1990 | Johnson et al. ............ 73/25.03 |
| 5,063,081 A * | 11/1991 | Cozzette et al. ................ 435/4 |
| 5,155,340 A * | 10/1992 | Morita et al. ................ 219/543 |
| 5,367,283 A * | 11/1994 | Lauf et al. ..................... 338/34 |
| 5,759,493 A | 6/1998 | Raisanen ..................... 422/88 |
| 6,435,005 B1 * | 8/2002 | Kikuchi et al. ............ 73/25.01 |

\* cited by examiner

*Primary Examiner*—Daniel S. Larkin
(74) *Attorney, Agent, or Firm*—Jordan M. Meschkow; Lowell W. Gresham; Meschkow & Gresham, PLC

(57) ABSTRACT

A gas sensor (22) for detecting the presence of a selected component in a gas (41) includes a substrate (28) exhibiting a low thermal resistance. A heater element (34) is disposed substantially over a surface area of a first surface (30) of the substrate (28). Sensor and reference elements (36, 38), formed from a single metal trace (54), are disposed on a second surface (32) of the substrate (28). The electrical resistivity of the sensor element (36) changes as the sensor element (36) adsorbs molecules of the selected component. During a regeneration process, the heater element (34) is activated to provide substantially even heating over the surface area of the first surface (30). Heat from the heater element (34) conducts through the substrate (28) to heat the sensor element (36) and the reference element (38) to a regeneration temperature sufficient to cause the adsorbed molecules of the selected component to be liberated.

20 Claims, 3 Drawing Sheets

THIN FILM GAS SENSOR

TECHNICAL FIELD OF THE INVENTION

The present invention relates to sensors for detecting the presence of selected components in a gaseous mixture. More specifically, the present invention relates to gas sensors that detect changes in the resistivity of thin film sensing elements caused by adsorption of gas molecules by the sensing elements.

BACKGROUND OF THE INVENTION

Gas sensors are useful for safety monitoring, process monitoring and control, evaluation of gaseous product quality, environmental control, and so forth. For example, mercury vapor and hydrogen sulfide gas sensors are used in a variety of industrial hygiene and process control applications.

Typically, miniature fuel cells, known as electro-chemical sensors, are used to detect hydrogen sulfide gas. Such electro-chemical sensors are known to have poor zero stability, a short life span, are temperature sensitive, and have problems with loss of sensitivity and calibration errors caused by interfering gasses. In addition, attempts to apply electro-chemical sensors to the detection of selected components at parts-per-billion (ppb) levels have not succeeded because of an excessively long time required for response, typically tens to hundreds of minutes. This excessive response time is undesirably slow for process control applications.

Optical gas sensors depend on measuring the transmission of light at a different wavelength for each gas. The particular wavelength identifies the gas and the amount of light absorbed by the gas determines the gas concentration. Conventional optical gas sensors are large, complicated, expensive, and can encompass a cabinet full of several discrete components which are usually hand-selected and hand-assembled. Attempts have been made to build the optical components, i.e., emitter, filter, and detector, on a single silicon chip. While the silicon chip based optical gas sensors are an improvement over prior art optical gas sensors in terms of size, they still suffer from fragility, excessive cost, poor sensitivity, and instability.

Thin film gas sensors have also been developed to detect a selected component in a composite gas. A thin film gas sensor is formed of a suitable semiconductor material whose electrical resistivity changes in response to the adsorption of the selected component. One such thin film gas sensor includes a gold thin metal film layer deposited on a ceramic substrate. The resistivity of the gold changes in response to the adsorption of mercury or hydrogen sulfide. The electrical resistance of the gold film exposed to the gas is measured and provides a basis for determining the concentration of the selected component.

Adsorptive thin film gas sensors are typically regenerated after adsorbing a sufficient amount of the selected component to trigger an indication circuit. Regeneration of the thin film involves heating the thin film to liberate the molecules of the selected component adsorbed by the thin film layer, i.e., the gold film, to prepare the gas sensor for a new cycle of gas detection and measurement. Depending upon the type of molecules adsorbed, the regeneration temperature can exceed 250° C. In prior art devices, the thin film layer is commonly used in both the sensing role and as a heater conductor for regeneration. Thin film gas sensors in which the thin film layer is used in both the sensing and heating roles are referred to hereinafter as combined sensor/heater thin film gas sensors.

Combined sensor/heater thin film gas sensors have been moderately successful in that they are typically more sensitive and more resistant to interference than electro-chemical and optical gas sensors. Unfortunately, combined sensor/heater thin film gas sensors suffer from a short life span. A principal failure mechanism involves the electromigration of the gold metal in the sensing film.

Electromigration is mass transport due to momentum exchange between conducting electrons and diffusing metal atoms. The result of electromigration is that metal atoms move from the thin gold film into the dividing layers on a chip. If electromigration occurs to a great degree, and enough metal atoms move into the dividing layers, the thin gold film may become too thin, resulting in failure of the gas sensor.

Electromigration is characteristic of metals at very high current density and temperatures of 100° C. or more. Accordingly, electromigration is exacerbated when the thin film layer is used in both the sensing role and as a heater conductor. Consequently, catastrophic failure of the combined sensor/heater thin film gas sensor occurs after a relatively small number of cycles of sensing and regeneration due to the high regeneration temperature.

In addition to the problem of electromigration, combined sensor/heater thin film gas sensors suffer from a lower than desired sensitivity. The sensitivity of a combined sensor/heater thin film gas sensor is governed by its geometric design. In particular, the life span of such a sensor is inversely proportional to the width of the thin gold film. The aspect ratio of a thin film gas sensor is the length of the sensor trace divided by the width of the sensor trace. In order to tolerate the high regeneration temperatures, the aspect ratio must be low, i.e., a thick width relative to the length. A low aspect ratio limits the sensitivity of the combined sensor/heater thin film gas sensor to parts-per-million levels, rather than ppb levels.

Yet another problem with combined sensor/heater thin film gas sensors is that the resistance of the sensor/heater trace is high. Therefore, a high voltage (approximately 60–100 volts) is needed to regenerate the sensor. Consequently, the combined sensor/heater thin film gas sensors are often limited to use in areas where 120 VAC or suitable power generators are available.

Some prior art thin film gas sensors circumvent the aforementioned problems found with combined sensor/heater thin film gas sensors by utilizing external heating elements to heat the thin metal film to the regeneration temperature. Unfortunately, such external heating elements can be difficult to manufacture and to calibrate for specific sensor applications. Moreover, the amount of heat generated by such a heating element may vary over the surface of the sensing layer. Uneven heating is undesirable because it can cause insufficient or inconsistent regeneration.

Yet other prior art thin film gas sensors have been fabricated to include an integrally formed heater element. One such thin film gas sensor includes a silicon substrate and a silicon nitride membrane supported by the substrate. A thin gold sensor trace and a thin gold reference trace are deposited on the silicon nitride membrane and progress in a substantially parallel spaced relationship relative to one another. Air cavities are formed in the substrate under the silicon nitride membrane, such that the membrane forms a number of platforms suspended above the cavities. The sensor and reference traces are located on each platform. A heater element is supported on the platforms above the upper surface of the silicon nitride membrane, but below the sensor element. The air cavities prevent heat produced in the heater element from escaping into the substrate. In other words, the air cavities act as a barrier so that the heat is directed to the sensor trace for efficient regeneration of the sensor trace.

The use of a separate embedded heater mitigates the problem of electromigration as discussed above, and enables a relatively even distribution of heat to the upper surface of the membrane. However, problems associated with this design include complexity and excessive cost of manufacture, as well as, fragility. In particular, the thin silicon nitride membrane is easily fractured during manufacturing and handling.

SUMMARY OF THE INVENTION

Accordingly, it is an advantage of the present invention that an improved thin film gas sensor for detecting the presence of a selected component is provided.

It is another advantage of the present invention that a thin film gas sensor is provided for detecting very low concentrations of a selected component.

Another advantage of the present invention is that a thin film gas sensor is provided that is capable of substantially even heating during regeneration.

Yet another advantage of the present invention is that a thin film gas sensor is provided that is robust, and is readily and cost effectively manufactured.

The above and other advantages of the present invention are carried out in one form by a device for detecting a presence of a selected component in a gas. The device includes a substrate having a first surface and a second surface, the substrate exhibiting a low thermal resistance. A heater element is disposed on the first surface. A sensor element and a reference element are located on the second surface. The sensor element is configured to adsorb molecules of the selected component, and the reference element is configured to adsorb the molecules of the selected component at a substantially lower rate than the sensor element.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
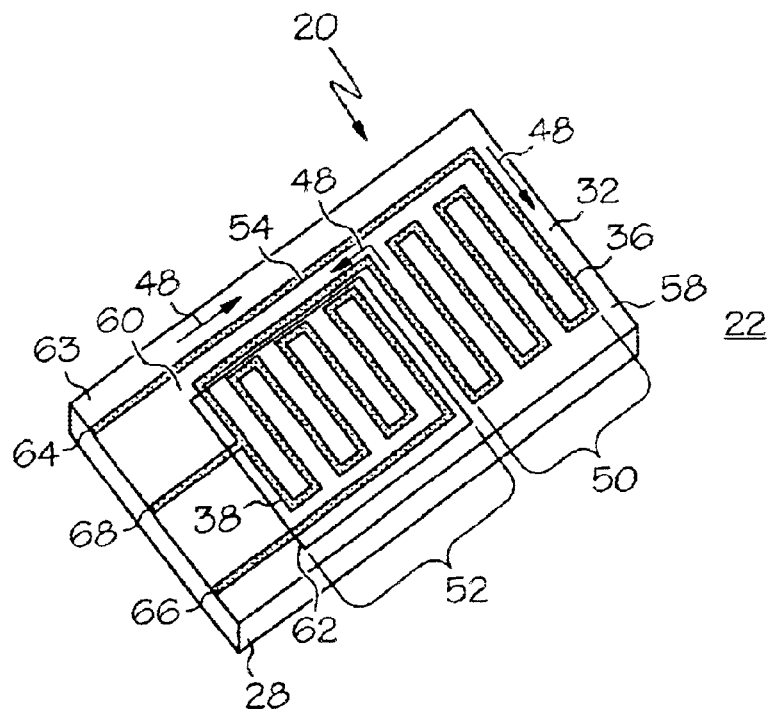
FIG. 1 shows a perspective view of a sensing side of a thin film gas sensor in accordance with a preferred embodiment of the present invention.
Figure 2:
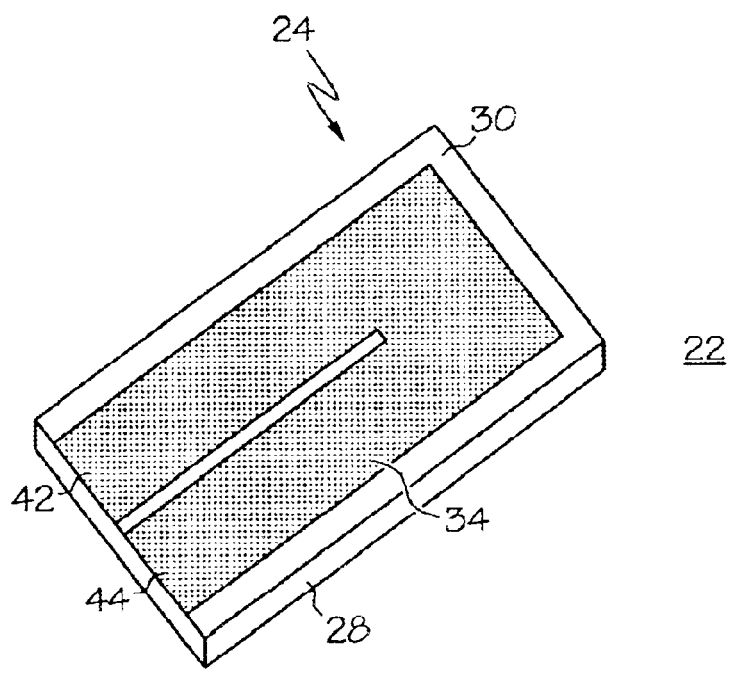
FIG. 2 shows a perspective view of a heating side of the thin film gas sensor of FIG. 1.
Figure 3:
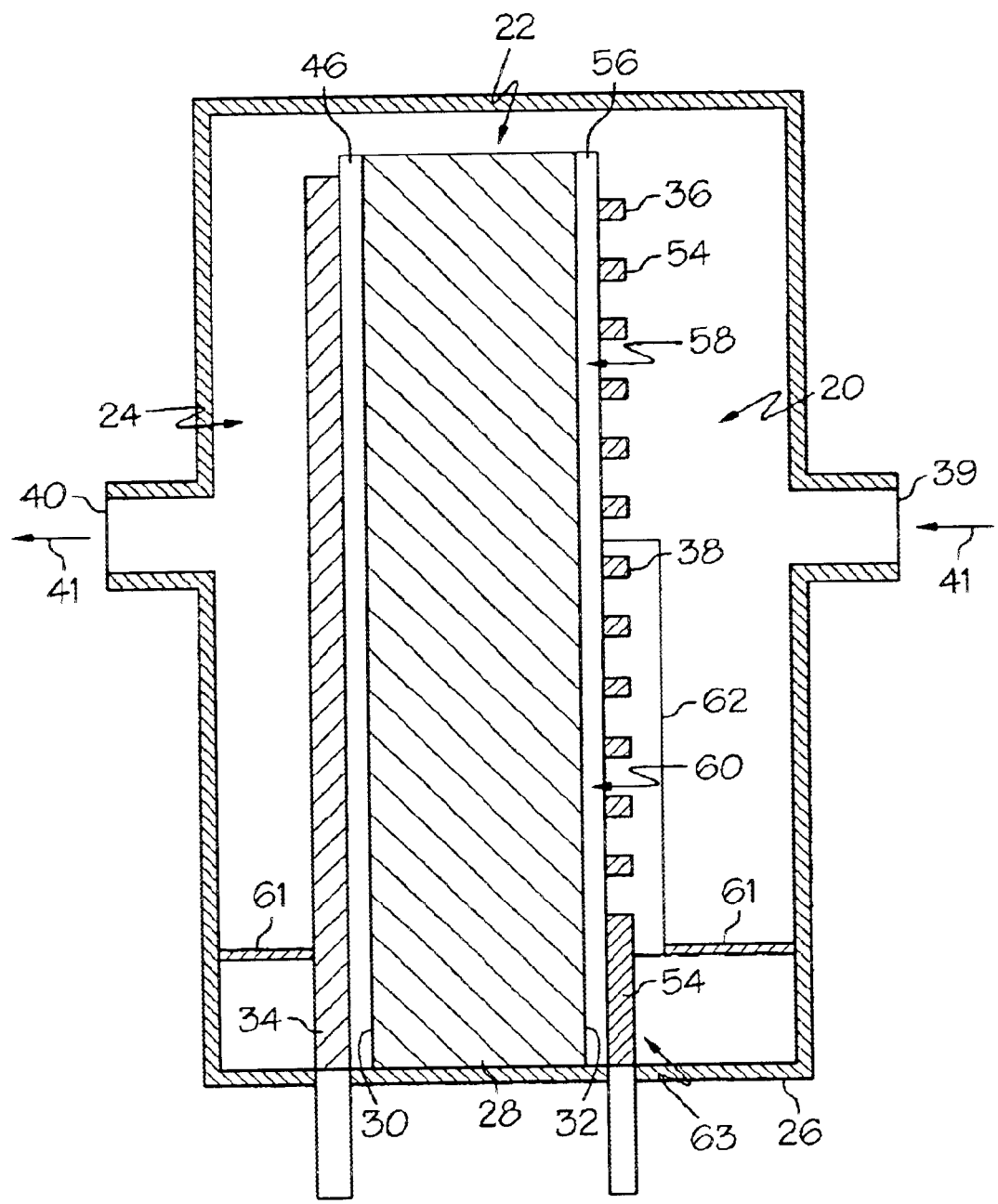
FIG. 3 shows a sectional side view of the thin film gas sensor surrounded by an exemplary enclosure.

Referring to FIGS. 1–3, FIG. 1 shows a perspective view of a sensing side 20 of a thin film gas sensor 22 in accordance with a preferred embodiment of the present invention. FIG. 2 shows a perspective view of a heating side 24 of thin film gas sensor 22, and FIG. 3 shows a sectional side view of thin film gas sensor 22 surrounded by an exemplary enclosure 26. Gas sensor 22 is configured to detect the presence of a specified component (such as, mercury vapor or hydrogen sulfide vapor) within a gas (such as, air). For purposes of the following discussion, the "specified component" is mercury or hydrogen sulfide vapor and the "gas" is air. Of course, the present invention need not be limited to the detection of mercury or hydrogen sulfide vapor or the analysis of air samples. Rather, those skilled in the art will recognize that gas sensor 22 may be adapted such that other gases or compounds may be monitored.

Thin film gas sensor 22 generally includes a substrate 28, having a first surface 30 and a second surface 32. A heater element 34 is disposed on first surface 30 to form heating side 24 of sensor 22. A sensor element 36 and a reference element 38 are located on second surface 32 to form sensor side 20 of sensor 22. Enclosure 26 includes an inlet port 39 and an exit port 40. Air, represented by arrows 41, enters through inlet port 39, flows around gas sensor 22, and exits via exit port 40. Sensor element 36 is configured to adsorb molecules of a selected component, such as, mercury or hydrogen sulfide vapor, from air 41 passing over sensing side 20 of gas sensor 22. In contrast, reference element 38 is configured to adsorb molecules of the selected component at a substantially lower rate than sensor element 36.

Substrate 28 exhibits a low thermal resistance. Thermal resistance is a measure of the difficulty with which heat conduction takes place along a material sample. As such, heat conducts readily through a material having low thermal resistance, and heat conducts poorly through a material having a high thermal resistance. In the present invention, heat from heater element 34 on first surface 30 readily conducts through substrate 28 to second surface 32 to heat sensor element 36 during a regeneration process, discussed below.

In a preferred embodiment, substrate 28 is formed from alumina ceramic. Alumina ceramic is a hard, zero porosity ceramic material typically used for high temperature, high wear resistant components. Alumina ceramic can be readily joined to itself and other metals through thin or thick film technology. In addition, the ceramic material readily conducts heat from heater element 34 to second surface 32.

Heater element 34 is a conductive trace having a first contact pad 42 and a second contact pad 44. First and second contact pads 42 and 44, respectively, couple to a heater control element, discussed in connection with FIG. 4. An adhesion layer 46 is deposited on first surface 30. Adhesion layer 46 facilitates the adhesion of heater element 34 to first surface 32 of substrate 28. In a preferred embodiment, adhesion layer 46 is deposited on first surface 30 using conventional evaporation techniques. Adhesion layer 46 may be formed from molybdenum, titanium, tungsten, titanium-tungsten alloy, or another refractory metal that does not significantly affect the resistivity of heater element 34. Heater element 34 is subsequently disposed over adhesion layer 46 by metal deposition utilizing conventional sputtering, vacuum evaporation and/or thick film paste deposition methodologies.

In a preferred embodiment, heater element 34 is a wide trace of electrically conductive gold that is disposed substantially over a surface area of first surface 30 of substrate 28. As such, when heater element 34 is activated during a regeneration process, heater element 34 imparts heat substantially evenly over first surface 32 of substrate 28. Through the use of heater element 34 on first surface 30 with conduction of heat through substrate 28 to sensor element 36 during regeneration, sensor element 36 need not perform both the sensor and heater roles. Accordingly, the problem of sensor failure due to electromigration that was experienced in prior art thin film gas sensors is mitigated.

In addition, since heater element 34 is separate from sensor element 36, heater resistance is low. Consequently, a much lower voltage can be utilized to regenerate gas sensor 22 than prior art devices. For example, gas sensor 22 may be regenerated using 10–20 volts, rather than the 60–100 volts required of prior art gas sensors. The lower regeneration voltage requirement of gas sensor 22 enables it to utilize battery power rather than 120 VAC power. Thus, gas sensor 22 can be utilized in areas where 120 VAC or a suitable power generator is unavailable.

Sensor element 36 and reference element 38 follow a contiguous path 48. In particular, sensor element 36 forms a first portion 50 of contiguous path 48, and reference element 38 forms a second portion 52 of contiguous path 48. To fabricate contiguous path 48, a single metal trace 54 is deposited on second surface 32 of substrate 28. Metal trace 54 has a chemical affinity for the selected component to be detected. For example, metal trace 54 may be gold. Gold is desirable for the detection of mercury and hydrogen sulfide vapor because gold is capable of adsorbing molecules of such gases.

An adhesion layer 56 is deposited on second surface 32 for facilitating the adhesion of metal trace 54 to second surface 32 of substrate 28. As discussed in connection with adhesion layer 46, adhesion layer 56 may be deposited on second surface 32 using conventional evaporation techniques. Furthermore, adhesion layer 56 may be formed from molybdenum, titanium, tungsten, titanium-tungsten alloy, or another refractory metal that does not affect the resistivity of metal trace 54. Metal trace 54 is subsequently disposed over adhesion layer 56 by metal deposition utilizing conventional sputtering and/or vacuum evaporation methodologies.

Contiguous path 48 follows a generally serpentine course. The serpentine course of path 48 is desirable to achieve an adequate resistance through metal trace 54 while reducing the size of gas sensor 22. However, the precise shape of contiguous path 48 may be selected according to physical packaging considerations and/or the desired electrical characteristics of gas sensor 22.

In a preferred embodiment, second surface 32 of substrate 28 includes a first region 58 and a second region 60 located on an opposing side of second surface 32 relative to first region 58. First portion 50 of contiguous path 48 of metal trace 54 is deposited in first region 58. Thus, sensor element 36 is located at first region 58 of second surface 32. Similarly, second portion 52 of contiguous path 48 of metal trace 54 is deposited in second region 60 so that reference element 38 is located at second region 60 of second surface 32.

Reference element 38, i.e., second portion 52 of contiguous path 48, is configured such that the presence of mercury or hydrogen sulfide vapor does not measurably alter the electrical resistivity of reference element 38. In other words, reference element 38 is less capable of adsorbing molecules of mercury or hydrogen sulfide vapor than sensor element 36, and any adsorption of such molecules by reference element 38 occurs at a substantially lower level than the adsorption of such molecules by sensor element 36. Accordingly, a gas impermeable coating 62 is deposited on second portion 52 of contiguous path 48.

Gas impermeable coating 62 causes reference element 38 to be less capable of adsorbing molecules of the selected component, i.e., mercury and hydrogen sulfide vapor, than sensor element 36. Gas impermeable coating 62 functions to insulate reference element 38 from mercury and hydrogen sulfide vapors without otherwise affecting the resistivity of metal trace 54 of reference element 38.

In a preferred embodiment, gas impermeable coating 62 is a polyimide. Polyimide is a synthetic polymeric resin of a class resistant to high temperatures, wear, and corrosion. A polyimide material is preferred because it is readily silk screened onto second surface 32 at second region 60 where it subsequently cures. However, other materials may be utilized to form gas impermeable coating 62. Other materials include, for example, glass, ceramic glazes, silicon nitride, and other materials that fulfill the criteria of gas impermeability, compatibility with the metal used to form metal trace 54, and compatibility with the material used to form substrate 28. In addition, gas impermeable coating 62 must withstand temperatures of approximately 260° C., which is the temperature required to liberate molecules of hydrogen sulfide vapor from gold during regeneration.

The deposition of a single metal trace 54 on substrate 28 simplifies the layout and deposition of the thin film layer of gas sensor 22 over prior art devices having pairs of sensor and reference traces. Moreover, the subsequent formation of sensor element 36 in first region 58 and reference element 38 in second region 60, through the deposition of gas impermeable coating 62 in second region 60, represents another simplification of fabrication over prior art devices where the sensor and reference elements progress in a substantially parallel spaced relationship relative to one another. Accordingly gas sensor 22 is readily and inexpensively manufactured.

In addition, since sensing element 36 does not perform both the sensor and heater roles, the aspect ratio of metal trace 54 is permitted be to quite high. In particular, the ratio of the length of metal trace 54 relative to the width of metal trace 54 is on the order of two hundred to five hundred. The aspect ratio of two hundred to five hundred for gas sensor 22 is significantly greater than the aspect ratio of approximately fifty needed to tolerate the high regeneration temperatures of the prior art combined sensor/heater thin film gas sensors. A high aspect ratio advantageously enables gas sensor 22 to detect molecules of the selected component, i.e., mercury or hydrogen sulfide vapor at parts-per-billion levels.

An insulating wall 61 of enclosure 26 separates sensing and heating sides 20 and 24, respectively, from a circuit interface edge 63 of gas sensor 22. Gas sensor 22 includes a sensor contact pad 64, a reference contact pad 66, and a ground contact pad 68 located along circuit interface edge 63. Sensor contact pad 64 is in electrical communication with sensor element 36 of metal trace 54 and reference contact pad 66 is in electrical communication with reference element 38 of metal trace 54. Ground contact pad 68 is further in electrical communication with metal trace 54 at an approximate junction of sensor and reference elements 36 and 38, respectively. Sensor contact pad 64, reference contact pad 66, and ground contact pad are used to interconnect gas sensor 22 to circuitry forming a resistance bridge for measuring the resistance changes caused by the adsorption of molecules of the selected component onto sensor element 36.

Figure 4:
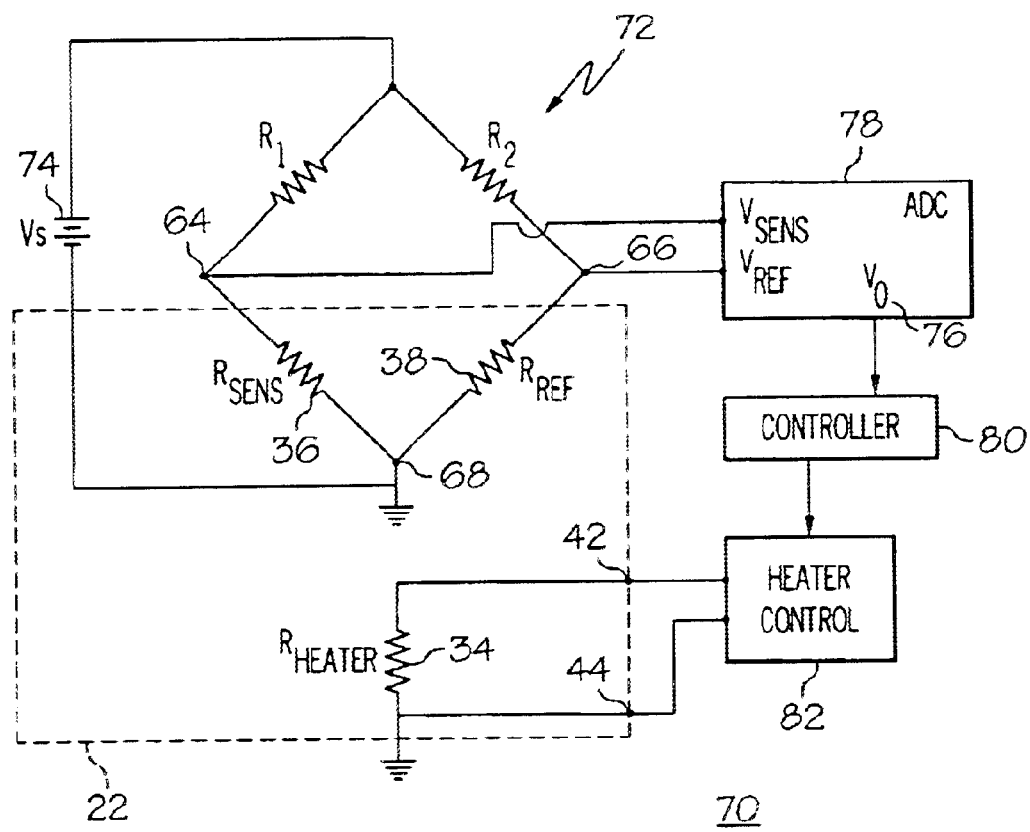
FIG. 4 shows a wiring diagram of an exemplary system used to detect and measure resistance changes due to the adsorption of a selected component by the thin film gas sensor.

FIG. 4 shows a wiring diagram of an exemplary system 70 used to detect and measure resistance changes due to the adsorption of a selected component by thin film gas sensor 22. A resistance bridge 72, typically referred to as a Wheatstone bridge, is formed to include electrical connectivity with sensor contact pad 64, reference contact pad 66, and ground contact pad 68 of gas sensor 22. Resistance bridge 72 includes four resistances, $R_1$, $R_2$, $R_{SENS}$, and $R_{REF}$ arranged in a diamond. $R_{SENS}$ represents the resistivity of sensor element 36, and $R_{REF}$ represents the resistivity of reference element 38.

A source voltage, $V_S$, 74 is supplied across the vertical diagonal of the diamond. An output voltage, $V_o$, 76 appears across the pair of terminals connected along the horizontal diagonal. This pair of terminals corresponds to sensor contact pad 64 and reference contact pad 66. Thus, output voltage 76 is a difference between the voltage ($V_{SENS}$) seen at sensor contact pad 64 and the voltage ($V_{REF}$) seen at reference contact pad 66. Resistance bridge 72 is readily employed to measure the resistance change of gas sensor 22 caused by the absorption of molecules of the selected component onto sensing side 20 (FIG. 1) of substrate 28.

In an exemplary embodiment, resistance bridge 72 is in electrical communication with an analog-to-digital converter (ADC) 78. ADC 78 receives output voltage 76, converts output voltage 76 into a digital signal, which is subsequently communicated to a controller 80 of exemplary system 70. Changes in output voltage 76 result from a change in resistance, i.e., difference between $R_{SENS}$ and $R_{REF}$, due to the adsorption of molecules of the selected component at sensor element 36.

In a sensing instrument, gas sensor 22 is arranged to have a sample of air 41 (FIG. 3) applied periodically to sensing side 20. Each measurement episode fractionally raises the electrical resistivity, $R_{SENS}$, of sensor element 36. When the electrical resistivity, $R_{SENS}$, reaches a predetermined resistivity threshold, heater element 34 (FIG. 2) is activated by a voltage applied via a heater control element 82 applied across first and second contact pads 42 and 44, respectively, (FIG. 2) of heater element 34. Voltage is applied for a time sufficient to conduct through substrate 28 and cause sensor element 36 to increase in temperature such that all adsorbed gas molecules are evaporated from sensor element 36. Mercury molecules begin releasing from sensor element 36 at a temperature of roughly 170° C., and hydrogen sulfide molecules begin releasing at a temperature of roughly 260° C. The heating voltage is removed following the liberation of the adsorbed gas molecules, and gas sensor 22 is allowed to cool to its operating temperature, whereupon the measurement cycle begins anew.

In summary, the present invention teaches of a thin film gas sensor for detecting the presence of a selected component, such as mercury and/or hydrogen sulfide vapor. Through the implementation of a separate sensor element and heater element, the sensor element is configured to have a high aspect ratio. This high aspect ratio enables detection of very low concentrations of the selected component, i.e., at parts-per-billion levels. Moreover, separation of the sensing and heating roles mitigates the problems of sensor failure due to electromigration, allows regeneration to be performed at low power levels, and enables the use of a large heater element that provides substantially even heating across the surface of the substrate during regeneration. Moreover, the single metal trace configuration over a substantially flat substrate is less fragile than prior art devices, and is readily and cost effectively manufactured.

Although the preferred embodiments of the invention have been illustrated and described in detail, it will be readily apparent to those skilled in the art that various modifications may be made therein without departing from the spirit of the invention or from the scope of the appended claims. For example, nothing limits the present invention to the detection of mercury or hydrogen sulfide gases. Rather, the other metals may be employed for the thin film gas sensor element, which have a chemical affinity for the particular vapor to be detected. For example, silver may be suitable for the detection of iodine vapor.

What is claimed is:

1. A device for detecting a presence of a selected component in a gas, said device comprising:
   a substrate having a first surface and a second surface, said substrate exhibiting a low thermal resistance;
   a heater element adhered to said first surface;
   a sensor element located on said second surface, said sensor element being configured to adsorb molecules of said selected component; and
   a reference element located on said second surface, said reference element being configured to adsorb said molecules of said selected component at a substantially lower rate than said sensor element.

2. A device as claimed in claim 1 wherein said substrate is alumina ceramic.

3. A device as claimed in claim 1 wherein said heater element is a conductive trace disposed over and substantially covering a surface area of said first surface of said substrate.

4. A device as claimed in claim 1 further comprising an adhesion layer deposited on said first surface for facilitating adhesion of said heater element to said substrate.

5. A device as claimed in claim 1 further comprising an adhesion layer deposited on said second surface for facilitating adhesion of said sensor element and said reference element to said substrate.

6. A device as claimed in claim 1 wherein said sensor element and said reference element follow a contiguous path, said sensor element forming a first portion of said contiguous path, and said reference element forming a second portion of said contiguous path.

7. A device as claimed in claim 6 further comprising:
   a metal trace deposited on said second surface of said substrate to form said contiguous path, said metal trace having a chemical affinity for said selected component; and
   a gas impermeable coating deposited on said second portion of said contiguous path, said gas impermeable coating causing said reference element to be less capable of adsorbing molecules of said selected component than said sensor element.

8. A device as claimed in claim 7 wherein said metal trace is gold.

9. A device as claimed in claim 7 wherein an electrical resistivity of said metal trace is impervious to said gas impermeable coating.

10. A device as claimed in claim 7 wherein said gas impermeable coating is polyimide.

11. A device as claimed in claim 1 wherein said second surface of said substrate comprises:
   a first region at which said sensor element is deposited; and
   a second region at which said reference element is deposited, said second region being located on an opposing side of said second surface relative to said first region.

12. A device as claimed in claim 1 wherein said heater element is activated to heat said substrate, said sensor element, and said reference element to a regeneration temperature sufficient to cause said molecules of said selected component to be liberated from said sensor element.

13. A device as claimed in claim 1 wherein an electrical resistivity of said sensor element changes when said molecules of said selected component are adsorbed by said sensor element, and said heater element is activated when said electrical resistivity reaches a predetermined resistivity threshold.

14. A device for detecting a presence of a selected component in a gas, said device comprising:

a substrate having a first surface and a second surface, said substrate exhibiting a low thermal resistance;

a heater element formed as a conductive trace and disposed over and substantially covering a surface area of said first surface;

a sensor element located on said second surface, said sensor element being configured to adsorb molecules of said selected component; and a reference element located on said second surface, said reference element being configured to adsorb said molecules of said selected component at a substantially lower rate than said sensor element, said heater element being activated to heat said substrate, said sensor element, and said reference element to a regeneration temperature sufficient to cause said molecules of said selected component to be liberated from said sensor element.

15. A device as claimed in claim 14 wherein an electrical resistivity of said sensor element changes when said molecules of said selected component are adsorbed by said sensor element, and said heater element is activated when said electrical resistivity reaches a predetermined resistivity threshold.

16. A device as claimed in claim 14 wherein said substrate is alumina ceramic.

17. A device as claimed in claim 14 wherein said sensor element and said reference element follow a contiguous path, said sensor element forming a first portion of said contiguous path, and said reference element forming a second portion of said contiguous path.

18. A device as claimed in claim 14 wherein said second surface of said substrate comprises:

a first region at which said sensor element is deposited; and a second region at which said reference element is deposited, said second region being located on an opposing side of said second surface relative to said first region.

19. A device for detecting a presence of a selected component in a gas, said device comprising:

a substrate having a first surface and a second surface, said substrate exhibiting a low thermal resistance;

a heater element adhered to said first surface;

a sensor element deposited in a first region on said second surface, said sensor element being configured to adsorb molecules of said selected component; and a reference element deposited in a second region on said second surface, said second region being located on an opposing side of said second surface relative to said first region, said reference element being configured to adsorb said molecules of said selected component at a substantially lower rate than said sensor element, said sensor element and said reference element following a contiguous path, said sensor element forming a first portion of said contiguous path, and said reference element forming a second portion of said contiguous path.

20. A device as claimed in claim 19 further comprising:

a metal trace deposited on said second surface of said substrate to form said contiguous path, said metal trace having a chemical affinity for said selected component; and a gas impermeable coating deposited on said second portion of said contiguous path, said gas impermeable coating causing said reference element to be less capable of adsorbing molecules of said selected component than said sensor element.

* * * * *